United States Patent
Lashinski et al.

(10) Patent No.: US 8,568,477 B2
(45) Date of Patent: *Oct. 29, 2013

(54) STENTLESS AORTIC VALVE REPLACEMENT WITH HIGH RADIAL STRENGTH

(75) Inventors: Randall T. Lashinski, Santa Rosa, CA (US); Gordon B. Bishop, Santa Rosa, CA (US)

(73) Assignee: Direct Flow Medical, Inc., Santa Rosa, CA (US)

( * ) Notice: Subject to any disclaimer, the term of this patent is extended or adjusted under 35 U.S.C. 154(b) by 1177 days.

This patent is subject to a terminal disclaimer.

(21) Appl. No.: 11/422,841

(22) Filed: Jun. 7, 2006

(65) Prior Publication Data

US 2007/0005133 A1    Jan. 4, 2007

Related U.S. Application Data

(60) Provisional application No. 60/688,305, filed on Jun. 7, 2005.

(51) Int. Cl.
*A61F 2/24* (2006.01)

(52) U.S. Cl.
USPC .......................................... 623/2.38; 623/2.17

(58) Field of Classification Search
USPC ............................. 623/2.12, 2.14, 2.17, 2.18
See application file for complete search history.

(56) References Cited

U.S. PATENT DOCUMENTS

| | | |
|---|---|---|
| 3,416,562 A | 12/1968 | Freeman et al. |
| 3,657,744 A | 4/1972 | Ersek |
| 3,671,979 A | 6/1972 | Moulopoulos |
| 3,714,671 A | 2/1973 | Edwards et al. |
| 4,035,849 A | 7/1977 | Angell et al. |
| 4,056,854 A | 11/1977 | Boretos et al. |
| 4,106,129 A | 8/1978 | Carpentier et al. |
| 4,183,102 A | 1/1980 | Guiset |
| 4,213,207 A | 7/1980 | Wilson |
| 4,221,548 A | 9/1980 | Child |
| 4,339,831 A | 7/1982 | Johnson |
| 4,592,340 A | 6/1986 | Boyles |
| 4,612,011 A | 9/1986 | Kautzky |
| 4,652,263 A | 3/1987 | Herweck et al. |
| 4,662,885 A | 5/1987 | DiPisa, Jr. |

(Continued)

FOREIGN PATENT DOCUMENTS

| | | |
|---|---|---|
| DE | 2700531 C2 | 4/1985 |
| EP | 2241284 A1 | 10/2010 |

(Continued)

OTHER PUBLICATIONS

U.S. Appl. No. 09/496,231, Jeffrey A. Hubbell et al., Biomaterials Formed by Nucleophilic Addition Reaction to Conjugated Unsaturated Groups, filed Feb. 1, 2000.

(Continued)

*Primary Examiner* — David Isabella
*Assistant Examiner* — Joshua Levine
(74) *Attorney, Agent, or Firm* — Knobbe, Martens, Olson & Bear, LLP

(57) ABSTRACT

Disclosed is a stentless transluminally implantable heart valve, having a formed in place support. The formed in place support exhibits superior crush resistance when compared to conventional balloon expandable or self expandable stent based valves.

4 Claims, 4 Drawing Sheets

(56) References Cited

U.S. PATENT DOCUMENTS

| | | |
|---|---|---|
| 4,727,873 A | 3/1988 | Mobin-Uddin |
| 4,750,488 A | 6/1988 | Wuchinich et al. |
| 4,750,901 A | 6/1988 | Molteno |
| 4,781,682 A | 11/1988 | Patel |
| 4,787,899 A | 11/1988 | Lazarus |
| 4,817,600 A | 4/1989 | Herms et al. |
| 4,827,911 A | 5/1989 | Broadwin et al. |
| 4,892,541 A | 1/1990 | Alonso |
| 4,922,902 A | 5/1990 | Wuchinich et al. |
| 4,931,047 A | 6/1990 | Broadwin et al. |
| 4,955,856 A | 9/1990 | Phillips |
| 4,960,424 A | 10/1990 | Grooters |
| 4,994,077 A | 2/1991 | Dobben |
| 5,015,227 A | 5/1991 | Broadwin et al. |
| 5,026,383 A | 6/1991 | Nobles |
| 5,032,128 A | 7/1991 | Alonso |
| 5,151,105 A | 9/1992 | Kwan-Gett |
| 5,163,897 A | 11/1992 | Persky |
| 5,163,953 A | 11/1992 | Vince |
| 5,167,628 A | 12/1992 | Boyles |
| 5,207,695 A | 5/1993 | Trout, III |
| 5,269,784 A | 12/1993 | Mast |
| 5,330,528 A | 7/1994 | Lazim |
| 5,360,444 A | 11/1994 | Kusuhara |
| 5,370,685 A | 12/1994 | Stevens |
| 5,370,691 A | 12/1994 | Samson |
| 5,397,351 A | 3/1995 | Pavcnik et al. |
| 5,411,552 A | 5/1995 | Andersen et al. |
| 5,423,851 A | 6/1995 | Samuels |
| 5,443,499 A | 8/1995 | Schmitt |
| 5,449,385 A | 9/1995 | Religa et al. |
| 5,500,014 A | 3/1996 | Quijano et al. |
| 5,534,024 A | 7/1996 | Rogers et al. |
| 5,554,180 A | 9/1996 | Turk |
| 5,554,185 A | 9/1996 | Block et al. |
| 5,578,034 A | 11/1996 | Estes |
| 5,616,149 A | 4/1997 | Barath |
| 5,649,978 A | 7/1997 | Samson |
| 5,690,570 A | 11/1997 | Chang et al. |
| 5,697,968 A | 12/1997 | Rogers et al. |
| 5,817,102 A | 10/1998 | Johnson et al. |
| 5,840,081 A | 11/1998 | Andersen et al. |
| 5,848,964 A | 12/1998 | Samuels |
| 5,855,601 A | 1/1999 | Bessler et al. |
| 5,871,537 A | 2/1999 | Holman et al. |
| 5,957,949 A | 9/1999 | Leonhardt et al. |
| 5,980,570 A | 11/1999 | Simpson |
| 6,007,575 A | 12/1999 | Samuels |
| 6,090,139 A | 7/2000 | Lemelson |
| 6,090,140 A | 7/2000 | Gabbay |
| 6,102,944 A | 8/2000 | Huynh et al. |
| 6,110,201 A | 8/2000 | Quijano et al. |
| 6,117,106 A | 9/2000 | Wasicek et al. |
| 6,126,007 A | 10/2000 | Kari et al. |
| 6,168,614 B1 | 1/2001 | Andersen et al. |
| 6,196,996 B1 | 3/2001 | Teirstein |
| 6,221,096 B1 | 4/2001 | Aiba et al. |
| 6,280,412 B1 | 8/2001 | Pederson, Jr. et al. |
| 6,299,637 B1 | 10/2001 | Shaolian et al. |
| 6,309,399 B1 | 10/2001 | Barbut et al. |
| 6,312,462 B1 | 11/2001 | McDermott et al. |
| 6,312,465 B1 | 11/2001 | Griffin et al. |
| 6,319,276 B1 | 11/2001 | Holman et al. |
| 6,371,970 B1 | 4/2002 | Khosravi et al. |
| 6,371,983 B1 | 4/2002 | Lane |
| 6,395,019 B2 | 5/2002 | Chobotov |
| 6,395,026 B1 | 5/2002 | Aboul-Hosn et al. |
| 6,409,759 B1 | 6/2002 | Peredo |
| 6,425,916 B1 | 7/2002 | Garrison et al. |
| 6,440,164 B1 | 8/2002 | Dimatteo et al. |
| 6,458,156 B1 | 10/2002 | Wan et al. |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,544,291 B2 | 4/2003 | Taylor |
| 6,562,069 B2 | 5/2003 | Cai et al. |
| 6,572,652 B2 | 6/2003 | Shaknovich |
| 6,582,462 B1 | 6/2003 | Andersen et al. |
| 6,602,286 B1 | 8/2003 | Strecker |
| 6,676,698 B2 | 1/2004 | McGuckin, Jr. et al. |
| 6,682,543 B2 | 1/2004 | Barbut et al. |
| 6,692,512 B2 | 2/2004 | Jang |
| 6,692,523 B2 | 2/2004 | Holman et al. |
| 6,719,788 B2 | 4/2004 | Cox |
| 6,719,789 B2 | 4/2004 | Cox |
| 6,733,525 B2 | 5/2004 | Yang et al. |
| 6,736,845 B2 | 5/2004 | Marquez et al. |
| 6,755,811 B1 | 6/2004 | Constantz |
| 6,761,733 B2 | 7/2004 | Chobotov et al. |
| 6,764,494 B2 | 7/2004 | Menz et al. |
| 6,767,362 B2 | 7/2004 | Schreck |
| 6,769,434 B2 | 8/2004 | Liddicoat et al. |
| 6,827,735 B2 | 12/2004 | Greenberg |
| 6,875,212 B2 * | 4/2005 | Shaolian et al. ............ 606/86 A |
| 6,890,353 B2 | 5/2005 | Cohn et al. |
| 6,896,690 B1 | 5/2005 | Lambrecht et al. |
| 6,936,057 B1 | 8/2005 | Nobles |
| 6,949,122 B2 | 9/2005 | Adams et al. |
| 6,958,212 B1 | 10/2005 | Hubbell et al. |
| 6,974,476 B2 | 12/2005 | McGuckin, Jr. et al. |
| 6,989,027 B2 | 1/2006 | Allen et al. |
| 6,994,093 B2 | 2/2006 | Murphy et al. |
| 7,018,406 B2 | 3/2006 | Seguin et al. |
| 7,037,334 B1 | 5/2006 | Hlavka et al. |
| 7,052,487 B2 | 5/2006 | Cohn et al. |
| 7,077,844 B2 | 7/2006 | Michelson |
| 7,077,862 B2 | 7/2006 | Vidlund et al. |
| 7,081,129 B2 | 7/2006 | Chobotov |
| 7,108,715 B2 | 9/2006 | Lawrence-Brown et al. |
| 7,112,219 B2 | 9/2006 | Vidlund et al. |
| 7,125,464 B2 | 10/2006 | Chobotov et al. |
| 7,150,758 B2 | 12/2006 | Kari et al. |
| 7,186,264 B2 | 3/2007 | Liddicoat et al. |
| 7,192,441 B2 | 3/2007 | Sherry |
| 7,201,772 B2 | 4/2007 | Schwammenthal et al. |
| 7,217,287 B2 | 5/2007 | Wilson et al. |
| 7,252,682 B2 | 8/2007 | Seguin |
| 7,255,711 B2 | 8/2007 | Holman et al. |
| 7,273,481 B2 | 9/2007 | Lombardo et al. |
| 7,276,078 B2 | 10/2007 | Spenser et al. |
| 7,309,340 B2 | 12/2007 | Fallin et al. |
| 7,320,704 B2 | 1/2008 | Lashinski et al. |
| 7,429,269 B2 | 9/2008 | Schwammenthal et al. |
| 7,435,257 B2 | 10/2008 | Lashinski et al. |
| 7,442,204 B2 | 10/2008 | Schwammenthal et al. |
| 7,445,630 B2 | 11/2008 | Lashinski et al. |
| 7,468,072 B2 | 12/2008 | Morsi |
| 7,491,230 B2 | 2/2009 | Holman et al. |
| 7,534,259 B2 | 5/2009 | Lashinski et al. |
| 7,534,261 B2 | 5/2009 | Friedman |
| 7,556,645 B2 | 7/2009 | Lashinski et al. |
| 7,585,321 B2 | 9/2009 | Cribier |
| 7,615,071 B2 | 11/2009 | Chobotov |
| 7,628,805 B2 | 12/2009 | Bash et al. |
| 7,641,686 B2 | 1/2010 | Lashinski et al. |
| 7,658,762 B2 | 2/2010 | Lashinski et al. |
| 7,666,193 B2 | 2/2010 | Starksen et al. |
| 7,666,220 B2 | 2/2010 | Evans et al. |
| 7,678,217 B2 | 3/2010 | Chobotov et al. |
| 7,682,383 B2 | 3/2010 | Robin |
| 7,726,943 B2 | 6/2010 | Stommel |
| 7,731,741 B2 | 6/2010 | Eidenschink |
| 7,744,912 B1 | 6/2010 | Hubbell |
| 7,762,943 B2 | 7/2010 | Khairkhahan |
| 7,766,954 B2 | 8/2010 | Chobotov et al. |
| 7,780,726 B2 | 8/2010 | Seguin |
| 7,785,365 B2 | 8/2010 | Holman et al. |
| 7,799,068 B2 | 9/2010 | Holman et al. |
| 7,846,203 B2 | 12/2010 | Cribier |
| 7,935,144 B2 | 5/2011 | Robin et al. |
| 8,002,826 B2 | 8/2011 | Seguin |
| 8,012,201 B2 | 9/2011 | Lashinski et al. |
| 8,016,877 B2 | 9/2011 | Seguin et al. |
| 8,057,540 B2 | 11/2011 | Cribier et al. |

(56) References Cited

U.S. PATENT DOCUMENTS

| | | |
|---|---|---|
| 8,070,805 B2 | 12/2011 | Vidlund et al. |
| 8,092,525 B2 | 1/2012 | Eliasen et al. |
| 8,133,213 B2 | 3/2012 | Lashinski |
| 8,142,497 B2 | 3/2012 | Friedman |
| 8,197,534 B2 | 6/2012 | Brumleve et al. |
| 2001/0007956 A1 | 7/2001 | Letac et al. |
| 2001/0021872 A1 | 9/2001 | Bailey et al. |
| 2002/0082689 A1 | 6/2002 | Chinn |
| 2002/0095116 A1 | 7/2002 | Strecter |
| 2002/0123802 A1 | 9/2002 | Snyders |
| 2002/0151961 A1 | 10/2002 | Lashinski et al. |
| 2002/0151970 A1 | 10/2002 | Garrison et al. |
| 2002/0183838 A1 | 12/2002 | Liddicoat et al. |
| 2002/0183841 A1 | 12/2002 | Cohn et al. |
| 2003/0023300 A1 | 1/2003 | Bailey et al. |
| 2003/0023303 A1 | 1/2003 | Palmaz et al. |
| 2003/0027332 A1 | 2/2003 | Lafrance et al. |
| 2003/0036795 A1 | 2/2003 | Andersen et al. |
| 2003/0040772 A1* | 2/2003 | Hyodoh et al. ............... 606/200 |
| 2003/0055496 A1 | 3/2003 | Cai et al. |
| 2003/0074058 A1 | 4/2003 | Sherry |
| 2003/0078654 A1 | 4/2003 | Taylor et al. |
| 2003/0083538 A1 | 5/2003 | Adams et al. |
| 2003/0093145 A1 | 5/2003 | Lawrence-Brown et al. |
| 2003/0125793 A1 | 7/2003 | Vesely |
| 2003/0125797 A1 | 7/2003 | Chobotov et al. |
| 2003/0130730 A1 | 7/2003 | Cohn et al. |
| 2003/0130731 A1 | 7/2003 | Vidlund et al. |
| 2003/0191527 A1 | 10/2003 | Shaknovich |
| 2003/0220684 A1 | 11/2003 | Holman et al. |
| 2003/0225453 A1 | 12/2003 | Murch |
| 2003/0233022 A1 | 12/2003 | Vidlund et al. |
| 2004/0003819 A1 | 1/2004 | St. Goar et al. |
| 2004/0030381 A1 | 2/2004 | Shu |
| 2004/0030382 A1 | 2/2004 | St. Goar et al. |
| 2004/0034320 A1 | 2/2004 | Burnett |
| 2004/0039442 A1 | 2/2004 | St. Goar et al. |
| 2004/0087975 A1 | 5/2004 | Lucatero et al. |
| 2004/0093060 A1 | 5/2004 | Seguin et al. |
| 2004/0116951 A1 | 6/2004 | Rosengart |
| 2004/0127979 A1 | 7/2004 | Wilson et al. |
| 2004/0148019 A1 | 7/2004 | Vidlund et al. |
| 2004/0148020 A1 | 7/2004 | Vidlund et al. |
| 2004/0167620 A1 | 8/2004 | Ortiz et al. |
| 2004/0176836 A1 | 9/2004 | Kari et al. |
| 2004/0186563 A1 | 9/2004 | Lobbi |
| 2004/0210304 A1 | 10/2004 | Seguin et al. |
| 2004/0225354 A1 | 11/2004 | Allen et al. |
| 2004/0249413 A1 | 12/2004 | Allen et al. |
| 2004/0249452 A1 | 12/2004 | Adams et al. |
| 2004/0254600 A1 | 12/2004 | Zarbatany et al. |
| 2004/0260322 A1 | 12/2004 | Rudko et al. |
| 2004/0260390 A1* | 12/2004 | Sarac et al. ............... 623/1.24 |
| 2005/0010285 A1 | 1/2005 | Lambrecht et al. |
| 2005/0021056 A1 | 1/2005 | St. Goar et al. |
| 2005/0021057 A1 | 1/2005 | St. Goar et al. |
| 2005/0033446 A1 | 2/2005 | Deem et al. |
| 2005/0055082 A1 | 3/2005 | Ben Muvhar et al. |
| 2005/0065550 A1 | 3/2005 | Starksen et al. |
| 2005/0090846 A1 | 4/2005 | Pedersen et al. |
| 2005/0107810 A1 | 5/2005 | Morales et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137695 A1 | 6/2005 | Salahieh et al. |
| 2005/0137696 A1 | 6/2005 | Salahieh et al. |
| 2005/0137699 A1 | 6/2005 | Salahieh et al. |
| 2005/0137701 A1 | 6/2005 | Salahieh et al. |
| 2005/0203549 A1 | 9/2005 | Realyvasquez |
| 2005/0203614 A1 | 9/2005 | Forster et al. |
| 2005/0209674 A1 | 9/2005 | Kutscher et al. |
| 2005/0209687 A1 | 9/2005 | Sitzmann et al. |
| 2005/0222488 A1 | 10/2005 | Rahdert et al. |
| 2005/0222489 A1 | 10/2005 | Rahdert et al. |
| 2005/0228422 A1 | 10/2005 | Rahdert et al. |
| 2005/0251251 A1 | 11/2005 | Cribier |
| 2005/0267574 A1 | 12/2005 | Cohn et al. |
| 2005/0273160 A1 | 12/2005 | Lashinski et al. |
| 2006/0004442 A1* | 1/2006 | Spenser et al. ............... 623/2.11 |
| 2006/0020327 A1 | 1/2006 | Lashinski et al. |
| 2006/0020332 A1 | 1/2006 | Lashinski et al. |
| 2006/0020333 A1 | 1/2006 | Lashinski et al. |
| 2006/0020334 A1 | 1/2006 | Lashinski et al. |
| 2006/0025750 A1 | 2/2006 | Starksen et al. |
| 2006/0025787 A1 | 2/2006 | Morales et al. |
| 2006/0025854 A1 | 2/2006 | Lashinski et al. |
| 2006/0025855 A1 | 2/2006 | Lashinski et al. |
| 2006/0041306 A1 | 2/2006 | Vidlund et al. |
| 2006/0063970 A1 | 3/2006 | Raman et al. |
| 2006/0074485 A1 | 4/2006 | Realyvasquez |
| 2006/0100699 A1 | 5/2006 | Vidlund et al. |
| 2006/0106449 A1 | 5/2006 | Ben Muvhar |
| 2006/0106450 A1 | 5/2006 | Ben Muvhar |
| 2006/0129025 A1 | 6/2006 | Levine et al. |
| 2006/0129051 A1 | 6/2006 | Rowe et al. |
| 2006/0129235 A1 | 6/2006 | Seguin et al. |
| 2006/0149135 A1 | 7/2006 | Paz |
| 2006/0178700 A1 | 8/2006 | Quinn |
| 2006/0190030 A1 | 8/2006 | To et al. |
| 2006/0212112 A1 | 9/2006 | Evans et al. |
| 2006/0217637 A1 | 9/2006 | Leiboff et al. |
| 2006/0229717 A1 | 10/2006 | Cohn et al. |
| 2006/0235512 A1 | 10/2006 | Brumleve et al. |
| 2006/0241656 A1 | 10/2006 | Starksen et al. |
| 2006/0252984 A1 | 11/2006 | Rahdert et al. |
| 2006/0271172 A1 | 11/2006 | Tehrani |
| 2006/0276874 A1 | 12/2006 | Wilson et al. |
| 2006/0276881 A1 | 12/2006 | Holman et al. |
| 2007/0005133 A1 | 1/2007 | Lashinski et al. |
| 2007/0027536 A1 | 2/2007 | Mihaljevic |
| 2007/0038293 A1 | 2/2007 | St.Goar et al. |
| 2007/0043435 A1 | 2/2007 | Seguin et al. |
| 2007/0050022 A1 | 3/2007 | Vidlund et al. |
| 2007/0055356 A1 | 3/2007 | Eidenschink |
| 2007/0093890 A1 | 4/2007 | Eliasen et al. |
| 2007/0142906 A1 | 6/2007 | Figulla et al. |
| 2007/0185566 A1 | 8/2007 | Khitin et al. |
| 2007/0185571 A1 | 8/2007 | Kapadia et al. |
| 2007/0203575 A1 | 8/2007 | Forster et al. |
| 2007/0213814 A1 | 9/2007 | Liddicoat et al. |
| 2007/0255399 A1 | 11/2007 | Eliasen et al. |
| 2007/0265700 A1 | 11/2007 | Eliasen et al. |
| 2007/0293943 A1 | 12/2007 | Quinn |
| 2008/0015687 A1 | 1/2008 | Lashinski et al. |
| 2008/0039881 A1 | 2/2008 | Greenberg |
| 2008/0039923 A1 | 2/2008 | Taylor et al. |
| 2008/0039935 A1 | 2/2008 | Buch et al. |
| 2008/0109073 A1 | 5/2008 | Lashinski et al. |
| 2008/0125860 A1 | 5/2008 | Webler et al. |
| 2008/0188923 A1 | 8/2008 | Chu |
| 2008/0194905 A1 | 8/2008 | Walsh |
| 2008/0208329 A1 | 8/2008 | Bishop et al. |
| 2008/0215143 A1 | 9/2008 | Seguin |
| 2009/0043382 A1 | 2/2009 | Maurer et al. |
| 2009/0048668 A1 | 2/2009 | Wilson et al. |
| 2009/0076600 A1 | 3/2009 | Quinn |
| 2009/0082857 A1 | 3/2009 | Lashinski et al. |
| 2009/0088836 A1 | 4/2009 | Bishop et al. |
| 2009/0131849 A1 | 5/2009 | Maurer et al. |
| 2009/0149949 A1 | 6/2009 | Quinn |
| 2009/0222084 A1 | 9/2009 | Friedman |
| 2009/0264984 A1 | 10/2009 | Chobotov |
| 2009/0318949 A1 | 12/2009 | Ganpath et al. |
| 2009/0319029 A1 | 12/2009 | Evans et al. |
| 2010/0004728 A1 | 1/2010 | Rao et al. |
| 2010/0010623 A1 | 1/2010 | Lashinski et al. |
| 2010/0016942 A1 | 1/2010 | Chobotov et al. |
| 2010/0016948 A1 | 1/2010 | Chobotov |
| 2010/0030204 A1 | 2/2010 | Stein et al. |
| 2010/0030327 A1 | 2/2010 | Chatel |
| 2010/0036360 A1 | 2/2010 | Herbowy et al. |

(56) References Cited

U.S. PATENT DOCUMENTS

| | | |
|---|---|---|
| 2010/0036485 A1 | 2/2010 | Seguin |
| 2010/0076481 A1 | 3/2010 | Stephens et al. |
| 2010/0106087 A1 | 4/2010 | Evans et al. |
| 2010/0168844 A1 | 7/2010 | Bergheim et al. |
| 2010/0256754 A1 | 10/2010 | Styrc |
| 2010/0292772 A1 | 11/2010 | Samuels |
| 2010/0324668 A1 | 12/2010 | Maurer et al. |
| 2011/0060407 A1 | 3/2011 | Ketai et al. |
| 2011/0066233 A1 | 3/2011 | Thornton et al. |
| 2011/0098802 A1 | 4/2011 | Braido et al. |
| 2011/0112625 A1 | 5/2011 | Ben-Muvhar et al. |
| 2011/0153009 A1 | 6/2011 | Navia et al. |
| 2011/0160846 A1 | 6/2011 | Bishop et al. |
| 2011/0213460 A1 | 9/2011 | Lashinski et al. |
| 2012/0016468 A1 | 1/2012 | Robin et al. |
| 2012/0022629 A1 | 1/2012 | Perera et al. |

FOREIGN PATENT DOCUMENTS

| | | |
|---|---|---|
| WO | WO 91/17720 | 11/1991 |
| WO | WO 93/01768 | 2/1993 |
| WO | WO 96/02212 | 2/1996 |
| WO | WO98/55047 | 12/1998 |
| WO | WO 00/41652 | 7/2000 |
| WO | WO 00/42950 | 7/2000 |
| WO | WO 01/06959 | 2/2001 |
| WO | WO 03/063740 | 8/2003 |
| WO | WO 03/096932 A1 | 11/2003 |
| WO | WO 2005/087140 A1 | 9/2005 |
| WO | WO 2005/107650 A2 | 11/2005 |
| WO | WO2009/144463 | 12/2009 |
| WO | WO2010/008548 | 1/2010 |
| WO | WO 2010117367 A1 | 10/2010 |
| WO | WO 2011/035154 | 3/2011 |
| WO | WO 2011033427 A1 | 3/2011 |
| WO | WO 2011105979 A1 | 9/2011 |
| WO | WO 2012/024428 | 2/2012 |

OTHER PUBLICATIONS

International Search Report for PCT Application No. PCT/US2005/015617 (the PCT counterpart of the parent application) filed May 5, 2005, mailed on Oct. 31, 2005, in 4 pages.

Written Opinion of the International Searching Authority for PCT Application No. PCT/US2005/015617 (the PCT counterpart of the parent application) filed May 5, 2005, in 7 pages.

International Search Report for PCT Application No. PCT/US2006/022112 filed Jun. 7, 2006, mailed on Mar. 19, 2007, in 1 page.

Written Opinion of the International Searching Authority for Application No. PCT/US2006/022112 filed Jun. 7, 2006, mailed on Mar. 19, 2007, in 4 pages.

European Search Opinion for Application No. EP06772431 filed Jun. 7, 2006, dated Nov. 6, 2008, in 3 pages.

Supplementary European Search Report for Application No. EP06772431 filed on Jun. 7, 2006, dated Nov. 6, 2008, in 2 pages.

International Search Report for PCT Application No. PCT/US2008/74104 filed Aug. 22, 2008, mailed on Dec. 24, 2008, in 3 pages.

Written Opinion of the International Searching Authority for Application No. PCT/US2008/74104 filed Aug. 22, 2008, mailed on Dec. 24, 2008, in 7 pages.

David et al., Aortic Valve Replacement with the Toronto SPV Bioprosthesis, *The Journal of Heart Valve Disease*, 1992, pp. 244-248, vol. 1(2), ICR Publishers.

Vyavahare et al., Prevention of Bioprosthetic Heart Valve Calcification by Ethanol Preincubation, *Circulation*, Jan. 21, 1997, pp. 479-488, vol. 95(2), American Heart Association.

European Examination Report for Application No. EP06772431 filed Jun. 7, 2006, dated May 3, 2009, in 1 page.

European Examination Report for corresponding EP 06772431.0, Feb. 3, 2010.

* cited by examiner

STENTLESS AORTIC VALVE REPLACEMENT WITH HIGH RADIAL STRENGTH

PRIORITY INFORMATION

This application claims priority under 35 U.S.C. §119 to U.S. Provisional Application Ser. No. 60/688,305, filed Jun. 7, 2005, the disclosure of which is incorporated in its entirety herein by reference.

BACKGROUND OF THE INVENTION

The malfunctioning of an aortic valve results in cardiac insufficiency and hence in a situation that is potentially fatal for the patient. For repair of such a defect, artificial aortic valves have been developed which are implanted as a substitute for the damaged valve in complex and risky open-heart surgery (sternotomy). The operation becomes particularly difficult when there is strong calcareous degeneration on the natural valve because painstaking attention must be paid during removal in order to ensure that calcification particles will not enter the blood circulation and cause there thromboses at other sites in the body. It is common to fasten the replacement valves—which are either mere engineering products or derived from porcine or other tissue valves—by suturing in the place of the removed valve.

There are numerous approaches in the development of methods simplifying this complex procedure of aortic-valve replacement in terms of both the surgical technique and the discomfort and strain for the patient, aiming at a minimally invasive technique of replacement of the aortic valve. In these approaches, the operation is performed via the femoral artery or even through the groin.

In view of the very restricted possibilities of access in the aortic arch, it is inevitable to adopt complex surgical strategies, firstly for explantation of the calcified aortic valve and secondly for implantation of an artificial valve in situ. Apart from all difficulties involved in the surgical operation—even though minimally invasive surgery is concerned that operates on advanced catheter technology—a maximum of concentration and above all a steady hand is demanded from the surgeon, specifically as the individual steps of surgical handling are within the millimeter range and there below. With the minimally invasive operation being performed with a sustained natural function of the heart, it is moreover important to carry out the operation as quickly as possible in order to keep the strain on the cardiac system at a minimum, which means that an operation of this kind is performed under a certain pressure in terms of time.

A special aspect is the ablation of the calcified aortic valve that must be removed completely from the aorta as quickly as possible, without lesion of adjoining unaffected tissue regions, specifically as the ablation involves mostly the application of mechanically acute cutting tools. Furthermore, it is important to ensure that severed tissue fragments or calcification particles will be extracted from the blood stream without any residues so as to avoid the occurrence of embolism or thromboses.

SUMMARY OF THE INVENTION

The present invention is based on the task of solving the problem configuring a device for replacement of an aortic or other valve on the human heart or peripheral vascular system by a minimally invasive technique. A device with a high radial strength may provide an ideal implant for heavily calcified aortic valves. Conventional treatment includes surgical replacement or a percutaneous balloon valvuloplasty. The second option is an insertion of a balloon catheter to the calcified aortic valve and inflation to dilation of the native valve to push the calcium aside. Though this technique is successful acutely, the restinosis rates are shown to be about 80% at twelve months. Some physicians in Europe believe this to be a technique to use in maintaining aortic flow in patients with out a surgical option. By this technique a patient may be treated with a balloon valvuloplasty up to three times providing an improved quality of life without a surgical intervention. It therefore stands to reason that during this acute restinosis after balloon valvuloplasty, if the calcium can be held back by a high radial strength device, a longer term therapy may be possible with a high strength device. This allows a larger patient population to be treated with a less invasive method and a more rapid recovery time. It may also eliminate the need for by-pass. This procedure may be completed under fluoroscopy, surface, transesophageal or transluminal echo. It will be desirable to monitor the patient's vital signs before, during and after the procedure. These may include blood pressures in relative chambers of the heart, aortic outflow, heart rate, breathing rates and blood chemistry. Blood thinners, heparin, aspirin and other drugs may be required to optimize blood before during and after the procedure.

Accordingly, one embodiment of the present invention comprises a cardiovascular prosthetic valve that includes an inflatable cuff. The cuff comprises at least one inflatable channel that forms, at least in part, a distal inflatable toroidal structure and a proximal inflatable toroidal structure. The inflatable cuff also comprises a waist that extends between the distal inflatable toroidal structure and the proximal inflatable toroidal structure. A valve is coupled to the inflatable cuff. The valve is configured to permit flow in a first axial direction and to inhibit flow in a second axial direction opposite to the first axial direction.

Another embodiment of the present invention comprises a prosthetic valve for replacing an aortic valve positioned between the left ventricle and the aorta of the heart. The valve includes an inflatable structure that has a distal end and a proximal end. A valve member is coupled to the inflatable structure. The valve member is positioned generally between the distal and proximal ends of the inflatable structure. The distal end of the inflatable structure is configured to be positioned within the left ventricle and the proximal end of the inflatable structure is configured to be positioned within the aorta.

Another embodiment of the present invention comprises a cardiovascular prosthetic valve that comprises an inflatable body. The inflatable body has at least a first inflatable chamber and a second inflatable chamber that is not in fluid communication with the first inflatable chamber. The inflatable body is to form, at least in part, a generally annular ring. A valve is coupled to the inflatable body. The valve is configured to permit flow in a first axial direction and to inhibit flow in a second axial direction opposite to the first axial direction. A first inflation port is in communication with the first inflatable chamber. A second inflation port is in communication with the second inflatable chamber.

Another embodiment of the present invention comprises a cardiovascular prosthetic valve that includes a cuff and an inflatable structure. The cuff has a distal end and a proximal end. The inflatable structure is coupled to the cuff and has at least one inflatable channel that forms a toroidal structure. A valve is coupled to the cuff. The valve is configured to permit flow in a first axial direction and to inhibit flow in a second axial direction opposite to the first axial direction. The distal end of the cuff has a non-circular cross-section with respect to the flow. The non-circular cross-section is configured to affect the performance of an adjacent valve.

Another embodiment of the present invention comprises a cardiovascular prosthetic valve that includes a flexible cuff having a distal end and a proximal end. An inflatable structure is coupled to the cuff and has at least one inflatable channel that forms a toroidal structure. A valve is mounted to the cuff. The valve is configured to permit flow in a first axial direction and to inhibit flow in a second axial direction opposite to the first axial direction. At least one anchor is moveable between a first position in which the anchor extends in a radial direction to engage an adjacent anatomical structure and a second position in which the anchor has a reduced radial profile.

Another embodiment of the present invention comprises a cardiovascular prosthetic valve that includes an inflatable body. A valve is coupled to the body. The valve is configured to permit flow in a first axial direction and to inhibit flow in a second axial direction opposite to the first axial direction. At least two control wires are detachably coupled to the inflatable body.

Yet another embodiment of the present invention comprises a cardiovascular prosthetic valve that includes an inflatable body comprising at least one inflation channel. A valve is coupled to the body. The valve is configured to permit flow in a first axial direction and to inhibit flow in a second axial direction opposite to the first axial direction. An inflation port is in communication with the at least one inflatable channel. A plug is positioned within the inflation port. An inflation tube extends through the inflation tube in communication with the at least one inflation channel. A balloon is coupled to the inflation tube. The balloon is configured to expand between a first, inflated position in which the balloon prevents the inflation tube from decoupling from the inflation port and a second, deflated position in which the inflation tube can be decoupled from the inflation port.

Another embodiment of the present invention comprises a method of implanting a prosthetic valve within a heart. A prosthetic valve comprising an inflatable structure is translumenally advanced to a position proximate a native valve of the heart. A portion of the inflatable structure that is distal to the native valve is inflated. A portion of the inflatable structure that is proximal to the native annular valve is inflated.

Another embodiment of the invention involves a method of implanting a prosthetic valve within the heart that comprises translumenally advancing a prosthetic valve that has an inflatable structure to a position proximate a native valve of the heart. A distal portion of the inflatable structure is inflated. The valve is proximally retracted to seat the distal portion of the inflatable structure against a distally facing portion of the native valve.

Another embodiment of the invention comprises a method of implanting a prosthetic valve within the heart. A prosthetic valve comprising an inflatable structure is advanced, translumenally, to a position proximate a native valve of the heart. A first chamber of the inflatable structure is inflated. A second chamber of the inflatable structure is independently inflated.

Another embodiment of the present invention relates to a method of implanting a prosthetic valve within the heart in which a prosthetic valve comprising an inflatable structure is advanced translumenally to a position proximate a native valve of the heart. The inflatable structure is inflated to deploy the prosthetic valve. The prosthetic valve is stapled or sutured to an adjacent anatomical structure.

Another embodiment of the present invention is a method of treating a patient. The method comprises translumenally advancing a prosthetic valve to a position proximate a native valve of the heart, fully deploying the prosthetic valve at the cardiovascular site, testing a performance characteristic of the prosthetic valve, at least partially reversing the deployment of the prosthetic valve, repositioning the prosthetic valve; and re-deploying the prosthetic valve.

Another embodiment of the present invention involves advancing a deployment catheter to a position proximate a native valve of the heart, the deployment catheter comprising an inflation tube and a prosthetic valve comprising an inflatable structure in communication with the inflation tube, inflating the inflatable structure with the inflation tube, removing the deployment catheter from the patient while the inflation tube remains coupled to the inflatable catheter, advancing a removal catheter over the inflation tube, deflating the inflatable structure, retracting the prosthetic valve into the removal catheter; and withdrawing the prosthetic valve and the removal catheter from the patient.

Another embodiment of the invention comprise a method of treating a patient that includes advancing a deployment catheter to a position proximate a native valve of the heart, the deployment catheter comprising a prosthetic valve and a linking member coupled to the prosthetic valve, deploying the prosthetic valve, removing the deployment catheter from the patient while the linking member remains coupled to the prosthetic valve, advancing a removal catheter over the linking member, retracting the prosthetic valve into the removal catheter; and withdrawing the prosthetic valve and the removal catheter from the patient.

Another embodiment of the present invention comprises identifying a patient with a minimum cross-sectional flow area through an aortic valve of no greater than 0.75 square cm, enlarging the minimum cross-sectional flow area through the valve; and deploying a prosthetic valve which provides a minimum cross-sectional flow area of at least about 1.75 square cm.

Yet another embodiment of the preset invention involves a method of treating a patient. The method comprises inflating an inflatable structure of a temporary valve at a cardiovascular site in fluid communication with a native valve, translumenally removing at least a portion of the native valve, deploying a prosthetic valve to compliment or replace a native valve, and removing the temporary valve.

Another embodiment of the present invention comprises a method of performing a procedure on a beating heart. In the method, a temporary valve is positioned in series fluid flow with a native valve. An inflatable prosthetic valve is deployed upstream of the temporary valve. The temporary valve is then removed.

Yet another embodiment of the present invention comprises a temporary heart valve catheter, for enabling minimally invasive procedures on a valve in a beating heart. The catheter includes an elongate, flexible catheter body, having a proximal end and a distal end, a valve on the distal end, the valve comprising an inflatable structure; and at least one link between the catheter and the valve to prevent detachment of the valve from the catheter.

Another embodiment of the present invention comprises a method of in situ formation of a prosthetic valve support. A prosthetic valve is attached to a flexible support component which is incapable of retaining the valve at a functional site in the arterial vasculature. The support component extends both proximally and distally of the base of the valve. The valve is positioned at the site. The flexible support component is supplemented to increase the rigidity of the support component sufficiently to retain the valve at the site.

Another embodiment of the present invention involves an implantable prosthetic valve that has an in situ formable support structure. The valve comprises a prosthetic valve, having a base and at least one flow occluder. A first flexible component is incapable of retaining the valve at a functional site in the arterial vasculature. The first component extends proximally of the base of the valve. A second flexible component is incapable of retaining the valve at a functional site in the arterial vasculature. The second component extends distally of the base of the valve. At least one rigidity component combines with at least one of the first and second flexible components to impart sufficient rigidity to the first or second components to retain the valve at the site.

There is provided in accordance with one embodiment of the present invention, a method of treating a patient. The method comprises deploying a temporary valve at a cardiovascular site in fluid communication with a native valve. At least a portion of the native valve is transluminally removed, and a prosthetic valve is deployed to complement or replace the native valve. The temporary valve is thereafter removed.

In one embodiment, the deploying a temporary valve step may comprise transluminally advancing the temporary valve to the site while the valve is in a first, reduced cross sectional configuration, and transforming the valve to a second, enlarged configuration to enable the valve to function at the site. The removing the temporary valve step may comprise transforming the valve in the direction of the first configuration, and transluminally removing the temporary valve. In certain embodiments, the temporary valve is permanently affixed to a temporary valve deployment catheter, to facilitate valve removal. The method may be accomplished on a beating heart.

The deploying a temporary valve step may comprise deploying a valve with tissue leaflets. Alternatively, the deploying a temporary valve step may comprise deploying a valve with synthetic leaflets. The valve may be supported within a self expandable stent, a balloon expandable stent, or an inflatable cuff. The removing the temporary valve step may comprise retracting the valve into a tubular sheath.

The transluminally removing at least a portion of the native valve step may comprise mechanically cutting native valve tissue. Mechanical cutting may be accomplished with an axially reciprocating cutter, or a rotational cutter. Cutting or decalcification may also be accomplished using a thermal source, such as a laser, or ultrasound.

The method may additionally comprise the step of capturing embolic material dislodged into the blood stream from the valve procedure. This may be achieved by filtration or extraction of the material through an aspiration process.

In accordance with another embodiment of the present invention, there is provided a method of performing a procedure on a beating heart. The method comprises the steps of positioning a temporary valve in series fluid flow with a native valve, and performing a procedure on the native valve. The temporary valve is thereafter removed. The valve may be the aortic valve, the mitral valve, or other valves. The procedure may be a valve repair, or a valve replacement.

In accordance with a another embodiment of the present invention, there is provided a temporary heart valve catheter, for enabling minimally invasive procedures on a valve in a beating heart. The catheter comprises an elongate flexible catheter body, having a proximal end and a distal end. A valve is carried by the distal end. At least one link is provided between the catheter and the valve to prevent detachment of the valve from the catheter. The valve may be supported by a support frame, which is connected to a pull wire or wires extending axially throughout the length of the catheter. Axial tensioning of the pull wire relative to the catheter body deploys the valve into its functional configuration. Proximal retraction of the pull wire causes the valve to reduce in cross section and draw into the distal end of the catheter, such as for placement or removal. The link may comprise a connection between the pull wire and a valve support.

In all of the foregoing embodiments, the formed in place stentless valve support of the present invention preferably retains essentially full functionality under a transverse load of at least about 2 lbs, often under loads of at least about 3 lbs, and in some cases loads of at least about 4 lbs. In some constructions of the present invention the stentless formed in place valve support will retain full functionality under transverse load of at least about 5 lbs. The formed in place valve support will preferably have a transverse displacement of no greater than about 0.2 inches, under a load of at least about 3 lbs, often at least about 4 lbs, and in certain embodiments in excess of about 6 lbs or 7 lbs.

Further features and advantages of the present invention will become apparent from the detailed description of preferred embodiments which follows, when considered together with the attached drawings and claims.

DETAILED DESCRIPTION OF THE PREFERRED EMBODIMENT

The present invention provides a percutaneous valve replacement with high radial strength.

Figure 2:
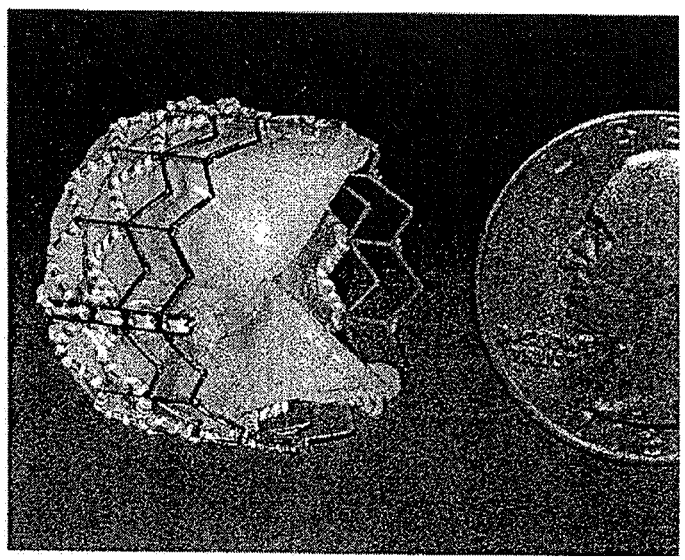
FIG. 2 is a front elevational perspective view of a balloon expandable stent based valve system.

One current method for implanting a tissue valve percutaneously includes a balloon expandable or self-expanding stent with a tissue valve attached as described in Andersen U.S. Pat. No. 6,168,614. See FIG. 2. Another method to implant a tissue valve percutaneously is described in U.S. Pat. No. 5,554,185 (Block), the disclosure of which is incorporated in its entirety herein by reference. One key feature in any valve apparatus is the ability to withstand forces generated by the closure of the valve at the commissural supports. In surgical valves these are seen as posts or pillars rising from the base of the device. General construction often includes a metallic frame encompassed with silicone and wrapped with Dacron. This frame will withstand the cyclical loading seen under normal conditions of operation in a heart valve. Since surgical valves are installed under direct visualization, the strength and materials can be different from those implanted percutaneously. By casting the support structure in-situ using a polymer, epoxy or hydrogel, the frame or lattice can be designed to withstand these forces long term as seen during normal operation within the body for years. These implantable medias may include such monoepoxys such as Phenol (EO)5 Glycol Ether (DENACOL EX-145), diepoxys such Ethylene Glycol Diglycidyl Ether (DENACOL EX-810), and polyepoxys such as Glycerol Polyglycidyl Ether (DENACOL EX-313) paired with amine compounds such as ethylenediamine (EDA), Diethylenetriamine (DETA), Aminoethylpiperazine (AEP), Aminoethylethanolamine (AEEA) or other compounds and epoxy groups available from companies such as Huntsman, Dixie Chemical, Alfa, Aesar, TCI America and Nagase ChemteX Corporation. Other compounds tested are available from Epoxy Technology include EOP-TEk 301 Part A and Part B. These above Medias all have advantages and disadvantages including favorable mechanical properties, water solulobility, biocompatibility, creep and fatigue resistance and viscosity characteristics that will aid in the development of a media that may be delivered via small bore catheter to an implant. Ideally the media would be a low viscosity, biocompatible fluid that may be sterilized, packaged and mixed in the catheterization lab with a set time that can be tailored to cure at approximately 37 degrees Centigrade in about 5 to no greater than about 30 or 45 minutes with mechanical properties that would include a resistance to fatigue and creep for an extended period of at least about 5 or 10 years but preferably at least about 20 years. It would additionally be ideal to have a water bourn-epoxy to aid in the biocompatibility and cytotoxicity of the media in case of a spill within the body so that neither embolic events nor neurological deficits would occur due to the introduction of this foreign material to the blood stream.

Figure 3A:
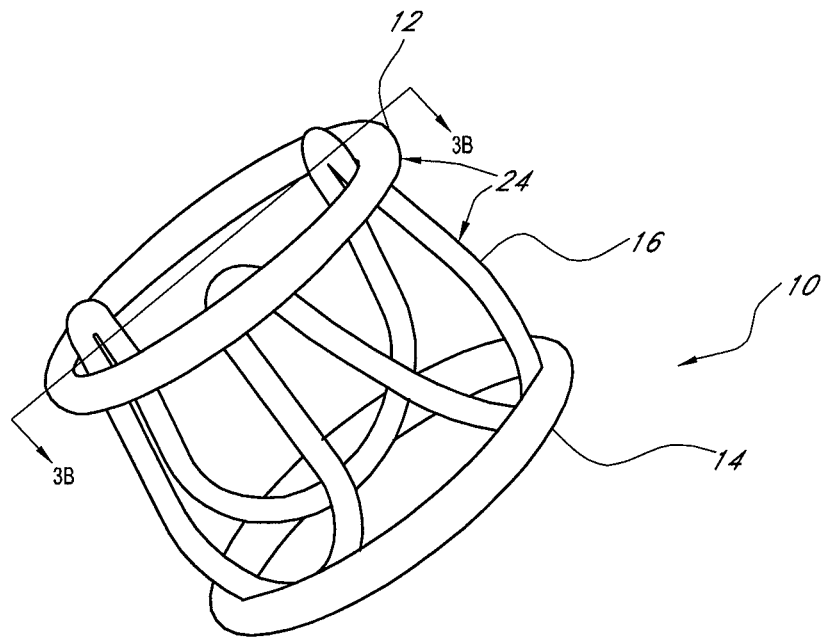
FIG. 3A is a perspective schematic view of a formed in place support in accordance with the present invention.
Figure 3B:
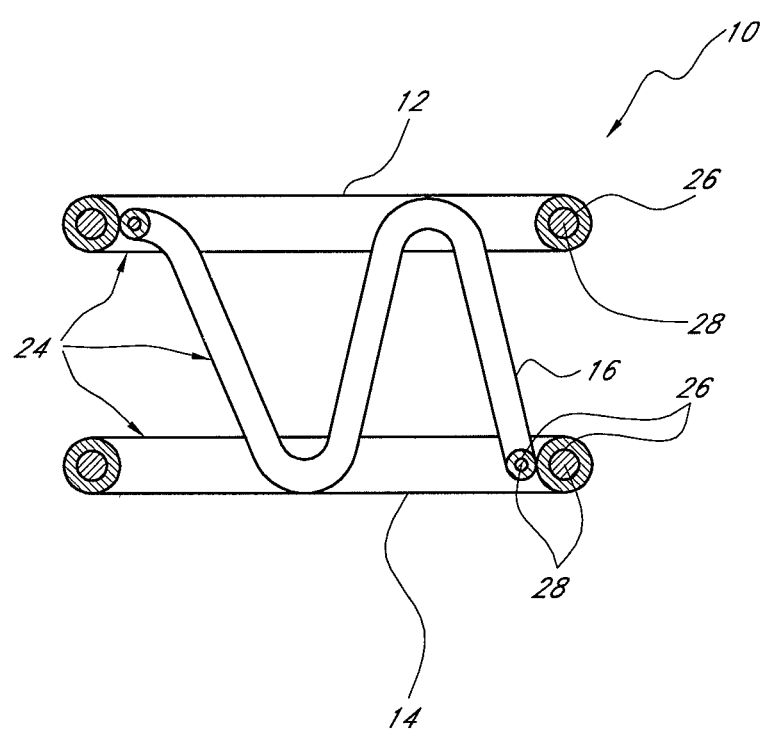
FIG. 3B is a cross sectional schematic view of the formed in place support of FIG. 3A.

Referring to FIGS. 3A and 3B, the valve support 10 generally comprises an inflatable cuff 24. The cuff 24 comprises at least one inflatable channel 26 that forms, at least in part, a first annular inflatable ring 12 spaced apart from a second annular inflatable ring 14. One or more inflatable channels 26 can be in fluid communication to create an inflatable chamber 28. Each of the rings 12 and 14 are adapted to be placed into communication with a deployment catheter, having at least one inflation chamber 28 for providing communication between the rings 12 and 14 and a source of inflation media. One or two or three or more generally axially extending struts 16, such as illustrated in FIG. 3A extend between the first and second rings 12 and 14. Struts 16 in FIG. 3A are illustrated in the form of a three pronged sinusoidal wave, to provide commissural support as is understood in the valve arts. The sinusoidal support 16 may also be inflated either simultaneously with or separately from either or both of the rings 12 and 14.

Figure 4:
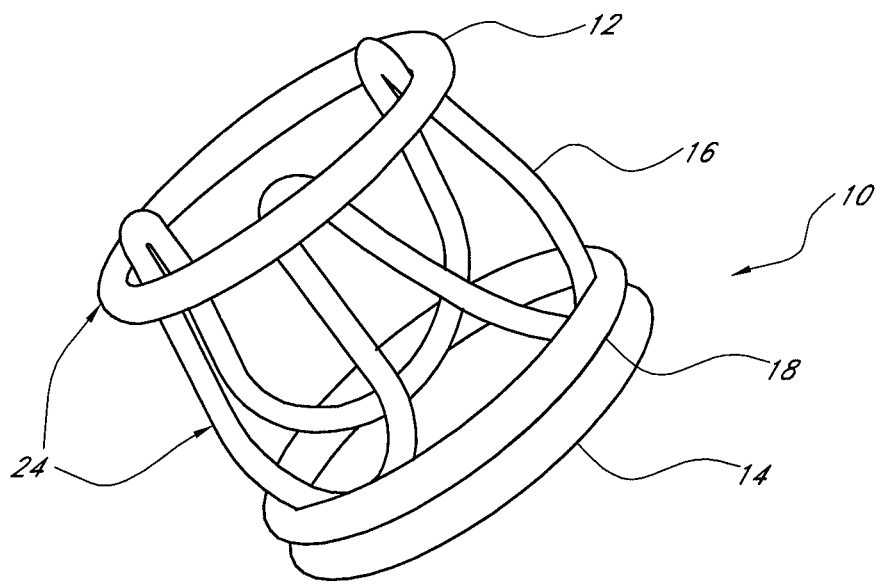
FIG. 4 is a perspective schematic view of an alternate formed in place support in accordance with the present invention.

Referring to FIG. 4, an inflatable valve support 10 is illustrated in which an additional annular ring 18 has been added at one end or both ends of the support 10. Inflatable support ring 18 may be in fluid flow communication with ring 14, and/or with the strut 16 and/or first ring 12. Alternatively, inflatable ring 18 may be provided with a separate inflation port and valve, such that it may be inflated independently of the remainder of the support 10.

Figure 5A:
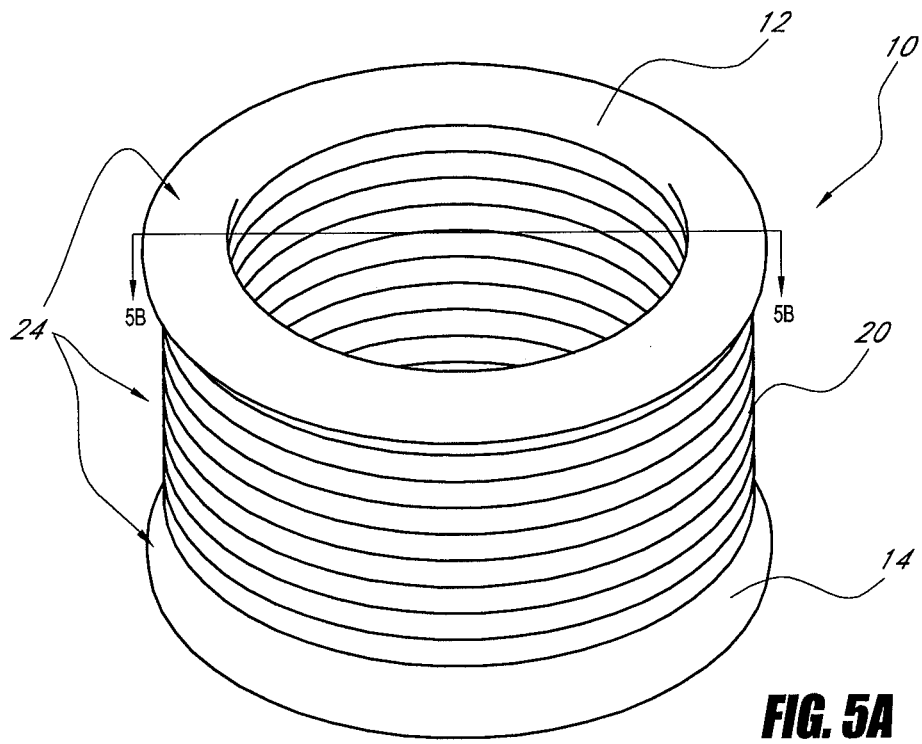
FIG. 5A is a perspective schematic view of an alternate formed in place support in accordance with the present invention.
Figure 5B:
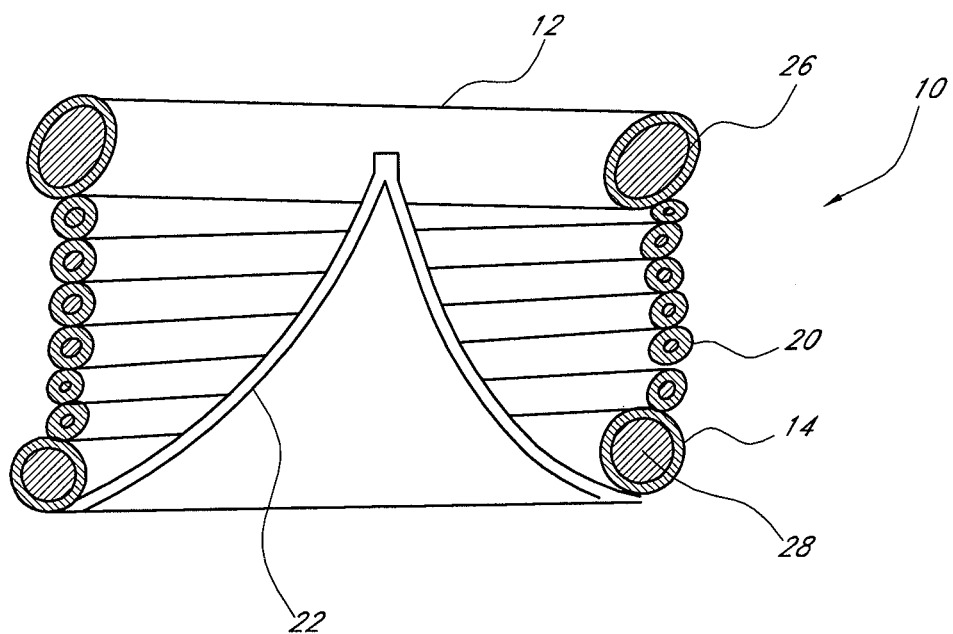
FIG. 5B is a cross sectional schematic view of the formed in place support of FIG. 5A.

Referring to FIG. 5A, there is illustrated a perspective schematic view of an alternate embodiment. FIG. 5B illustrates a schematic cross section of the embodiment of FIG. 5A. In this embodiment, the support 10 is provided with an inflatable cuff 24. The cuff 24 comprises at least one inflatable channel 26 that forms, at least in part, a first annular support 12 and second annular support 14. One or more inflatable channels 26 can be in fluid communication to create an inflatable chamber 28. A plurality of intermediate support rings 20 are provided, in between the first support 12 and the second support 14. Annular support 20 may be in the form of one or two or three or four or five or more annular rings. The rings 20 may be discrete rings stacked upon each other, or a continuous spiral as will be understood in the art. Rings 20 may be separately inflatable, or may be in fluid communication with either or both of the first support 12 and second support 14. FIG. 5B, a valve 22 is schematically illustrated as carried by the support 10.

The commissural supports can be attached directly or indirectly to a toroid or ring shape. Since the forces at the comissures during valve closure are inward and radial, the ring is in a compressive loading state and will withstand higher forces than a post-design as described above and as seen in a common surgical valve. Additionally, a balloon expandable or self-expanding stent is created to be radially expandable by design. For that same reason the stent may also be susceptible to radial crush and require a rather large cross sectional area to withstand similar loading conditions normally acceptable in a ring or toroid. The zigzag patterning normally seen in stent design prohibits large radial strength capabilities that may be required to safely mount and deliver percutaneously a tissue valve. An additional design to increase the radial strength of a tubular member is to increase the number of tubes or hoops. Rather than an upper and lower hoop additional hoops may be added between the two to increase the loading force per hoop. These may vary in cross sectional diameter to limit the area to which blood may flow past the valve leaflets. In this design the two distal hoops may have a large cross section of about 0.15 inches to about 0.05 inches and the middle hoops may have a smaller cross sectional diameter of 0.13 inches to 0.02 inches. The larger the cross sectional diameter the larger the load carrying capacity of the overall device in radial resistance and crush. The shape of these hoops may additionally be changed from a circular configuration to one of a clover or semi-triangular shape to accommodate the natural aortic valve shape. This may allow for more uniform fit but may also allow for less radial resistance in crush due to the irregular shape.

The stentless formed in place supports in accordance with the present invention are described in additional detail in U.S. patent application Ser. No. 11/122,983, filed May 5, 2005, entitled Transluminally Implantable Heart Valve With Formed In Place Support, the disclosure of which is incorporated in its entirety herein by reference. Measured in accordance with the technique described below, formed in place heart valves in accordance with the present invention exhibit superior crush resistance compared to balloon expandable and self expandable stent based valves. In general, balloon expandable stent based valves are believed to crush to a point where they would not operate properly under a transversely applied force as described below of less than 2 lbs. However, the formed in place stentless valve support of the present invention will retain essentially full functionality under a transverse load of 2 lbs., and, often under a load of at least about 3 lbs., and in some cases at least about 4 lbs., and for some constructions at least about 5 lbs. In certain designs in accordance with the present invention, the stentless formed in place valve support is subject to a reduction in diameter of less than 0.2 inches under a load of at least about 6 lbs., and, in some embodiments, at least about 7 lbs. or more. Deformation of no more than about 0.4 inches or no more than about 0.3 inches may also be achieved at the pressures recited above, depending upon the cuff design and inflation media. In the design described herein with the Epo-Tek 301 media the radial crush in a flat plate test will withstand forces in excess of about nine pounds of compressive force with no permanent deformation and about thirty percent temporary deflection. Other media tested such as 811 with an amine of DETA (Ethylene Glycol Digiycidyl Ether with a Diethylenetriamine) provide resistance to compressive loading as described above in the range of from about one to about three pounds. Within this range is where the ideal resistance to compressive loads may be ideal. This resistance to compression is mainly due to the re-narrowing of the aortic valve and the calcium that occurs on and within the valve leaflets. Therefore resistance to this closure is combated with a high radial strength device to allow the maximum orifice area possible.

Viewed from another perspective, the force in pounds applied by opposing plates aligned transversely to the longitudinal axis of a stent will cause a displacement (transverse crush) of the stent of at least about 0.2 inches under a load of less than about 2 lbs., and, often less than about 1 lb. In contrast, formed in place stentless valve supports in accordance with the present invention, require at least about 3 lbs., often at least about 4 lbs. or 5 lbs., and in certain embodiments in excess of 6 lbs. or 7 lbs. of transverse force in order to achieve a transverse displacement of 0.2 inches.

An experimental protocol and test data for a particular embodiment of the present invention is described below.

Figure 1:
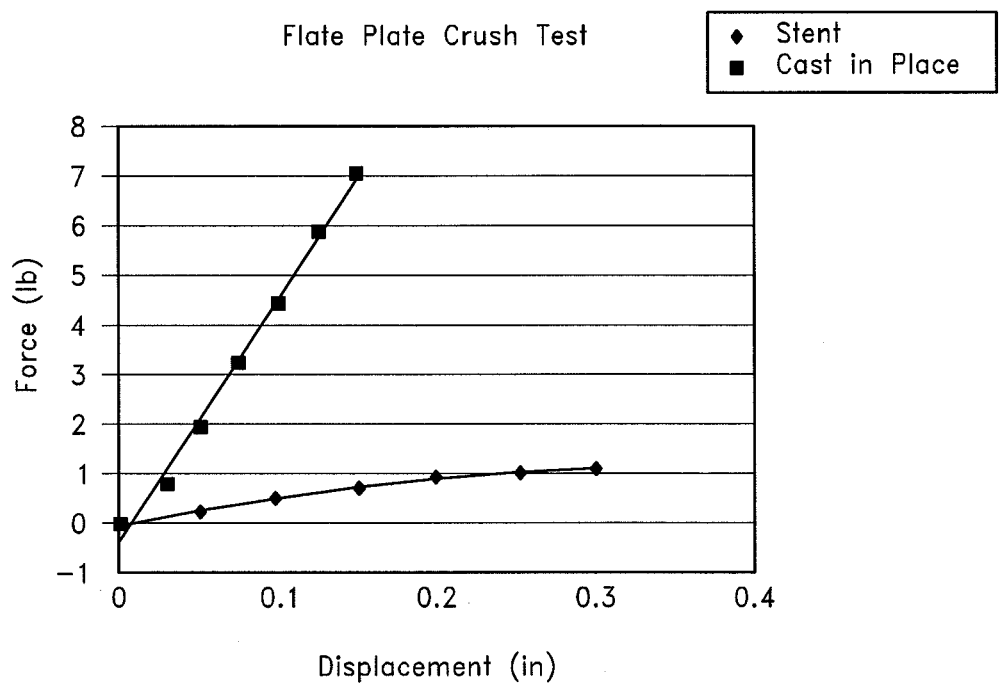
FIG. 1 illustrates the displacement or transverse crushing in inches, as a function of applied force, for a stent and a cast in place valve support.

Tests were performed using a force gauge system (Chatillion model TCD 200) where compressive loads were applied at various deflections to both stent-based structures and cast in-situ structures. The stent structure consisted of a 316L laser-cut stent with a zigzag patent similar to the device produced by Edwards/PVT and described in the Andersen U.S. Pat. No. 6,168,614. The strut thickness was 0.018 inches by 0.018 inches. The diameter was approximately 1.00 inches and the length was about 1.50 inches (see FIG. 1).

The cast in place structure had an outside diameter of about 1.00 inches and an axial length of about 0.63 inches. The geometry of the inflation channels includes an upper ring and a lower ring or toroid each of which measured about 0.09 inch in circular cross section (see FIG. 2). There were three additional independent sinusoidal elements to support the valve cusps that connected the upper and lower rings. All of these elements were sewn into a Dacron fabric which covered the inflation channels. The rings and sinusoidal elements were filled with a media (Epo-tek 301) from Epoxy Technologies 14 Fortune Drive Billerica, Mass. 01821 and allowed to cure.

Each device was set between two flat plates with the axial direction perpendicular to the force gauge. Between the two flat plates compressive radial forces were measured on the stainless steel laser-cut stent at 0.00 inches displacement and on up to 0.300 inches displacement in compression. Forces were measured from 0.00 lbs to 1.10 lbs respectively (see chart 1). Next the cast-in-place structure was tested in the same manner where displacements were measured from 0.00 inches to 0.149 inches. Forces were measured from 0.00 lbs to 7.05 lbs respectively (see chart 1). Clearly this shows a significantly higher radial strength of the formed in place support when compared to a stainless steel laser-cut stent system.

Tissue valves designed for surgical implantation have used polymer support structures in the past. The three commissural posts on these structures support the inward force exerted by the leaflets upon valve closure. This causes an alternating bending moment on the support posts, and as a result the polymer may be subject to creep.

The major difference between plastics and the more traditional materials is the time-dependent viscoelastic behavior of polymers. Plastic parts under load relax with time if they are maintained at a controlled deformation (stress relaxation), or they continue to deform if they are held under a constant load (creep).

Creep is the continued extension or deformation of a plastic part under continuous load. It results from the viscoelastic flow of the polymer with time.

Creep is probably the most widely studied long-term property. As a result there is an abundance of data available in the literature and from resin manufacturers. Creep data is usually expressed as "apparent creep modulus" as a function of the logarithm of time under constant load (assumed to be constant stress). Modulus is the ratio of stress over strain; therefore, apparent creep modulus is the constant stress divided by the actual measured strain (the deformation which changes with time).

Creep measurements are probably the easiest long-term tests to perform—one simply sets up the specimen, hangs a weight on it, and periodically measures and records the change in deflection. Tensile creep is probably the "purest" data, but it isn't the most common creep data available, most likely due to gripping and slippage difficulties. Compressive creep is reserved primarily for rubbers and elastomers where stress relaxation and compressive flow are important performance parameters for long-term service.

Flexural creep taken in a 3-point bend arrangement is most widely performed, generally because it is the easiest to set up and monitor. A rectangular plastic specimen is supported horizontally by two steel pins where and a weight is placed on the specimen at the midpoint of the two supports. A dial indicator at the location of the weight monitors the deflection with respect to time.

One limitation with flex creep is that it is not a "pure" stressed state. The constant stress is calculated as the maximum "fiber" stress that occurs directly under the load on the underside surface of the bar—this is the only point at which that maximum fiber stress exists. Actually, the stress distribution through the bar varies from tensile on the underside surface of the bar to compressive stress on the topside surface. The compressive stress tends to inhibit the overall deflection of the specimen.

Also, as the specimen deflects, the bar must move along the supports to accommodate the deflection. If the calculated fiber strain on the underside surface exceeds about 5%, a significant portion of the constant load is consumed as the driving force to "pull" the specimen through the supports—rather than merely bend the specimen. Therefore, the "constant" stress begins to decrease as the experiment continues.

In addition, at some strain level, probably around 5%, the actual strain on the bar at the point of loading stops increasing—no further curvature occurs in the central area of the specimen—but the specimen continues bend toward the ends of the bar as it slides through the supports. Inasmuch as the apparent fiber strain is calculated based on the amount of deflection from the original horizontal position, the method begins to yield erroneous data. Therefore, flexural creep experiments, although informative and easy to perform, can lead to somewhat conservative (optimistic) or even erroneous results. Care should be taken on the interpretation of these data.

Creep occurs in all plastic parts that are under stress. The higher the stress and the longer the part is under the stress dictates whether or not creep may be a significant factor in the performance of a part.

In order to control the amount of creep in a percutaneous cast in place polymer valve an upper ring is added connecting the support posts. This upper ring is able to support the loads imposed by the leaflets at a much lower stress than similarly sized support posts. The geometry described above is believed to provide sufficient radial strength at the point of commissural attachment that creep of the polymer support structure will not be an issue during the expected life of the valve (approximately 20 years).

Thus, one preferred geometry for the stentless formed in place valve supports in accordance with the present invention is to provide at least a first annular support which, in the assembled valve, will be located in the vicinity of the base or annulus for the valve, and a second annular support which, in the finished assembly will be in the vicinity of commissural supports for the valve. Connective elements will connect the first and second annular supports, such as the inflatable connective elements illustrated in FIG. 2. Alternatively, preformed connective elements such as polymeric struts, wire and/or fabric may be used. In addition, the formed in place commissural support ring may be attached to the commissural supports or in the vicinity of comissures in a conventional stent based transluminally implantable heart valve. Thus, the present invention additionally contemplates a hybrid structure in which the annulus or base support may comprise a balloon expandable stent or a self expandable stent, and crush resistance in the vicinity of the comissures or anatomically distal end of the stent is provided by a formed in place annular support as described herein.

We claim:

1. A cardiovascular prosthetic valve comprising:
a stentless support structure, the stentless support structure comprising an inflatable cuff comprising at least one inflatable channel that forms, at least in part, a distal inflatable toroidal structure and a proximal inflatable toroidal structure, the inflatable cuff also comprising a waist that extends between the distal inflatable toroidal structure and the proximal inflatable toroidal structure, wherein the inflatable cuff is transformable from a reduced cross sectional configuration for transluminal deployment to a functional enlarged configuration to form a flow path through the support structure;
a valve coupled to the inflatable cuff and positioned in the flow path, the valve configured to permit flow in a first axial direction and to inhibit flow in a second axial direction opposite to the first axial direction;
a hardenable media positioned within the inflatable cuff holding the inflatable cuff in the functional enlarged configuration; and
wherein the inflatable cuff in the functional enlarged configuration exhibits sufficient crush resistance that it will deform radially no more than about 0.3 inches under a load of about 4 pounds when the hardenable media in the inflatable cuff is hardened.

2. The cardiovascular prosthetic valve of claim 1, wherein the at least one inflatable channel includes a first chamber associated with the distal inflatable toroidal structure and a second, independent, chamber associated with the proximal inflatable toroidal structure.

3. A prosthetic valve for replacing an aortic valve positioned between the left ventricle and the aorta of the heart, the prosthetic valve comprising:
a stentless support structure, the stentless support structure comprising an inflatable structure comprising a distal end and a proximal end, wherein the inflatable structure is transformable from a reduced cross sectional configuration for transluminal deployment to a functional enlarged configuration surrounding a flow path for blood; and
a valve member coupled to the inflatable structure, the valve member being positioned generally between the distal and proximal ends of the inflatable structure and in the flow path for blood;
a hardenable media positioned within the inflatable structure holding the inflatable structure in the functional enlarged configuration;
wherein the distal end of the inflatable structure is configured to be positioned within the left ventricle and the proximal end of the inflatable structure is configured to be positioned within the aorta; and
wherein the inflatable structure in the functional enlarged configuration exhibits sufficient crush resistance that it will deform radially no more than about 0.3 inches under a load of about 4 pounds when the hardenable media is hardened.

4. The prosthetic valve of claim 3, wherein the inflatable structure includes a first chamber associated with the distal end and a second separate chamber associated with the proximal end.

* * * * *